United States Patent
Miller et al.

(10) Patent No.: US 6,201,129 B1
(45) Date of Patent: Mar. 13, 2001

(54) TRICYCLIC DERIVATIVES AND THEIR USE AS ANTI-CANCER AGENTS

(75) Inventors: David Drysdale Miller, Beckenham; Patrick Vivian Richard Shannon, South Glamorgan, both of (GB); Laddawan Chuncharprasert, Khon Kaen (TH)

(73) Assignee: Univ. College Cardiff Consultants, Cardiff (GB)

( * ) Notice: Subject to any disclaimer, the term of this patent is extended or adjusted under 35 U.S.C. 154(b) by 0 days.

(21) Appl. No.: 08/875,667

(22) PCT Filed: Feb. 1, 1995

(86) PCT No.: PCT/GB95/00203

§ 371 Date: Aug. 29, 1997

§ 102(e) Date: Aug. 29, 1997

(87) PCT Pub. No.: WO95/21171

PCT Pub. Date: Aug. 10, 1995

(51) Int. Cl.[7] ............ C07D 487/04; C07D 209/00; A61K 31/40
(52) U.S. Cl. ............ 548/433; 548/441; 514/454
(58) Field of Search .................. 548/433, 441; 514/454

(56) References Cited

PUBLICATIONS

Samoniya et al., (CA 93:204500, abstract of Khim. Geterotsikl. Soedin. (1980), (6), pp. 849–850).*
CAS online Print out, Beilstein Reg. No. (BRN), 319745.*
Chunchatprasert, Laddawan et al. (CA 125:275689, abstract of J. Chem. Soc., Perkin Trans, ! (1996), 15, p. 1787–1795.*

* cited by examiner

Primary Examiner—Sabiha Qazi
(74) Attorney, Agent, or Firm—Matthews, Collins, Shepherd & Gould, P.A.

(57) ABSTRACT

A compound having the formula

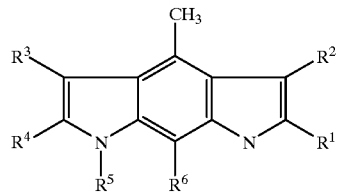

wherein $R^1$ is $COOR^8$ wherein $R^8$ is alkyl having from 1 to 10 carbon atoms or aralkyl, the aralkyl having from one to four carbon atoms in the alkyl portion and a carbocyclic or heterocyclic group in the aryl portion;

$R^2$ is H, alkyl having from 1 to 10 carbon atoms, or $COOR^7$ wherein $R^7$ is alkyl having from 1 to 10 carbon atoms;

$R^3$ is H, alkyl having from 1 to 10 carbon atoms, or $COOR^8$;

$R^4$ is H, alkyl having from 1 to 10 carbon atoms, or $COOR^8$;

$R^5$ is H, alkyl having from 1 to 10 carbon atoms, aralkyl having from 1 to 4 carbon atoms in the alkyl portion, aryl having from 1 to 10 carbon atoms, acyl having from 1 to 10 carbon atoms, or $COOCH_3$; and $R^6$ is H or $COOCH_3$;

and thereof.

11 Claims, No Drawings

TRICYCLIC DERIVATIVES AND THEIR USE AS ANTI-CANCER AGENTS

This application is a 371 of PCT/GB95/00203 filed on Aug. 1, 1997 (Priority (Feb. 1, 1995).

The present invention relates to heterocyclic compounds which have been found to have anti-tumour activity. More specifically, the invention concerns benzo[1,2-b:4,5-b'] dipyrroles, benzo[1,2-b:5,4-b']dipyrroles, cyclopent[f] indoles, benzo[1,2-b:4,5-b']difurans, benzo[1,2-b:5,4-b'] difurans, 2H-indeno[5,6-b]furans, benzo[1,2-b:4,5-b'] dithiophenes, benzo[1,2-b:5,4-b']dithiophenes, cyclopent[f] indenes and 5H-furo[2,3-f]indoles methods for their preparation, pharmaceutical formulations containing them and their use as anti-tumour agents.

Research in the area of cancer chemotherapy has produced a variety of anti-tumour agents, which have differing degrees of efficacy. Standard clinically used agents include adriamycin, actinomycin D, methotrexate, 5-fluorouracil, cis-platinum, vincristine and vinblastine. However, these presently available anti-tumour agents are known to have various disadvantages, such toxicity to healthy cells and resistance to certain tumour types.

There thus exists a continuing need to develop new and improved anti-tumour agents.

Khoshtariya et al, khim. Geterotsikl. Soedin (1982), (4) 304–7, disclose the synthesis of certain pyrroloindoles.

Gruenhaus H., J.Heterocyclic Chem. 13(6), 1161–3 discloses the synthesis of certain indenothiophenes.

There have now been discovered novel compounds which exhibit anti-tumour cell activity including a group of novel compounds which exhibit anti-tumour cell activity with low toxicity against normal cell lines.

Thus, in a first aspect the present invention provides a compound of the general formula (1)

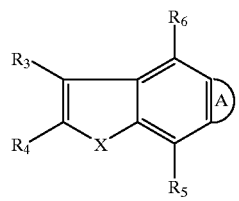

(I)

or a salt or physiologically functional derivative thereof, wherein A is

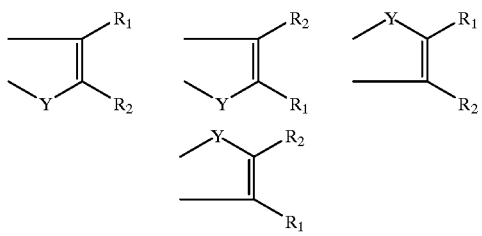

X is O, S, SO, SO$_2$, CH$_2$, CO or NR$^7$, wherein R$^7$ is H, alkyl, aralkyl, aryl, alkenyl, acyl, alkynyl, sulphonyl, substituted sulphonyl, or COOMe;

Y is O, S, SO, SO$_2$, CH$_2$, CO or NR$^7$;

R$^1$ is COR$^8$, CHO, CH$_2$OH, CH$_2$OR$^8$, CONH$_2$, COOR$^8$, CONHR$^8$, CONR$^8$R$^9$, CSOR$^8$, CSSR$^8$, COSR$^8$, CSNHR$^8$, CSNR$^8$R$^9$, CNHOR$^8$ wherein R$^8$ and R$^9$ are independently hydrogen, alkoxyalkyl, heterocycloalkyl, heteroaralkyl, or C$_{1-10}$ optionally substituted hydrocarbyl group which may optionally contain one or two oxygen atoms in the chain;

or R$^8$ and R$^9$ are a sugar group.

R$^2$ is H, halo, cyano, COOR$^8$, alkyl, aryl, alkenyl, alkynyl, alkoxy, (wherein alkyl, aryl, alkenyl, alkynyl and alkoxy can be substituted) or CH$_2$CH$_2$CO$_2$R$^{12}$ wherein R$^{12}$ is alkyl or aryl;

R$^3$ is H, alkyl, halogen, cyano, amino, COOR$^8$, CONHR$^8$, COR$^8$, CH$_2$OH, CH$_2$OR$^8$, CONH$_2$, CONR$^8$R$^9$, CSOR$^8$, CSSR$^8$, COSR$^8$, CSNHR$^8$, CSNR$^8$R$^9$ or CNHOR$^8$;

R$^4$ is H, halogen, cyano, amino, alkyl, COOR$^8$, CONHR$^8$, COR$^8$, CH$_2$OH, CH$_2$OR$^8$, CONH$_2$, CONR$^8$R$^9$, CSOR$^8$, CSSR$^8$, COSR$^8$, CSNHR$^8$, CSNR$^8$R$^9$ or CNHOR$^8$;

R$^5$ is H, hydroxy, aryloxy, aralkyloxy, alkyl, substituted alkyl, aralkyl, nitro, amino, halo, cyano, COOR$^8$ or CHO;

R$^6$ is H, aryl, alkyl, aralkyl, nitro, halogen, CHO or COR$^{13}$ wherein R$^{13}$ is alkyl or aryl; wherein R$^8$ is not H when R$^2$ is H and R$^3$ is not H or Me when A is

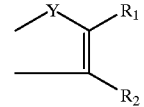

Alkyl groups present in general formula (I) may be straight or branched chain alkyl groups, and may contain 1–10 carbon atoms and suitably 1–6 carbon atoms. Examples of such alkyl groups include methyl, ethyl, t-butyl and the like.

Acyl groups may be straight or branched and may contain 1–10 carbon atoms and suitably 1–6 carbon atoms. Examples of such acyl groups include ethanoyl and propanoyl groups.

Alkoxy may be straight or branched and may contain 1–10 carbon atoms and suitably 1–6 carbon atoms. Examples of such alkoxy groups include methoxy, ethoxy, and the like.

Aryl includes both carbocyclic aryl groups and heterocyclic aryl groups normally containing a maximum of 10 ring atoms. Carbocyclic aryl groups include, for example, phenyl and naphthyl and contain at least one aromatic ring. Heterocyclic aryl groups include, for example, thienyl, furyl, pyridyl, indole and quinoline rings.

An aralkyl group may contain from 1 to 4 atoms in the alkyl portion and the aryl portion may be a carbocyclic or heterocyclic aryl group.

Cycloalkyl includes both cycloalkyl groups and heterocyclo alkyl groups normally containing between 3 and 6 ring atoms. Heterocycloalkyl groups include e.g. morpholino, thiomorpholino, piperidino, imidazolino, pyrrolidino, pyrazolidino, piperazino, tetrahydrofuranyl, tetrahydropyranyl.

When R$^8$ and R$^9$ are independently optionally substituted C$_{1-10}$ hydrocarbyl which may optionally contain one or two oxygen atoms in the chain this includes optionally substituted alkyl, hydroxyalkyl, alkenyl, alkynyl, carbamoylalkyl, alkoxyalkyl, cycloalkyl, cycloalkenyl, aralkyl, aryloxyalkyl.

Substituents which may be present on the C$_{1-10}$ hydrocarbyl group which may optionally contain one or two oxygen atoms in the chain include hydroxy, azido, alkenyl, halo, nitro (NO$_2$), amino, (optionally substituted by one or 2 alkyl groups), cyano, carboxylate, alkyl ester, aralkyl esters or aryl esters, (wherein the alkyl ester, aralkyl ester and aryl ester can be substituted) alkyl, aryl, aralkyl, aryloxy, aryalkoxy, substituted arylalkoxy, sulphinyl, sulphonyl, thio, alkylthio, alkoxy, hydroxyalkyl, halo alkyl, phosphate, phsophonate, silyl, silyloxy, (wherein silyl and silyloxy may be substituted by one or more $C_{1-6}$ alkyl or aryl) keto, and formyl. Substituents which may be present on alkyl esters, aralkyl esters and aryl esters include nitro, amino, hydroxy, alkoxy, halogen, cyano and alkyl.

Where $R^8$ is a sugar this group may be present in a protected or unprotected form. Preferred sugar-protecting groups include isopropylidene, benzylidene acetate, benzoyl, paranitrobenzyl, paranitrobenzoyl, benzyl, substituted silyl and tetrahydropyranyl.

When $R^8$ is a sugar such as a tetrose, pentose, hexose (including furanose and pyranose) or heptose, preferred sugars include glucose, fructose, mannose, ribose, arabinose.

Substituents which may be present on the sulphonyl and sulphinyl include alkyl, aryl and aralkyl.

Halogen represents fluoro, chloro, bromo or iodo.

X preferably represents NH, A is preferably

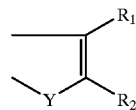

and Y preferably represents NH.

$R^1$ is preferably $COOR^8$, with $R^8$ preferably being alkyl or aralkyl.

$R^2$ is preferably H, alkyl, or $COOR^8$ wherein $R^8$ is preferably alkyl, $R^3$ is preferably alkyl, $R^4$ is preferably alkyl or $COOR^8$, $R^5$ is preferably hydrogen, and $R^6$ is preferably hydrogen or methyl, and salts and physiologically functional derivatives thereof.

One group of preferred compounds according to the present invention includes:

Ethyl 1,7-dihydro-3,4,6-trimethylpyrrolo[3,2-f]indole-2-carboxylate;

Diethyl 1,7-dihydro-3,4,6-trimethylpyrrolo[3,2-f]indole-2,5-dicarboxylate; and

Ethyl 6-methoxycarbonyl-3,4-dimethylpyrrolo[3,2-f]indole-2-carboxylate and physiologically functional derivatives thereof.

A second group of preferred compounds according to the invention include:

Ethyl 6-Benzyloxycarbonyl-3,4-dimethylpyrrolo[3,2-f]indole-2-carboxylate;

Dibenzyl 3,4-dimethylpyrrolo[3,2-f]indole-2,6-dicarboxylate;

Ethyl 7-methoxycarbonyl-3,4-dimethylpyrrolo[3,2-f]indole-2-carboxylate; and

Ethyl 3,4-dimethylpyrrolo[3,2-f]indole-2-carboxylate and physiologically functional derivatives thereof.

Compounds of the general formula (I) have been tested against two specially developed cell lines which are clones of the human fibrosarcoma cell-line HT1080. One clone HT1080scc2, retains the transformed phenotype of the parental line, whilst the other, HT1080lc, is a morphologically flat, non-tumourigenic, revertant.

According to a further aspect, the present invention also provides a process for preparing compounds of general formula (I), which process comprises the catalysed reaction of a compound of formula (II) with a compound of formula (III) in an inert solvent at a temperature between room temperature and the reflux temperature of the solvent, wherein X, Y, $R^1$, $R^2$, $R^3$ $R^4$, $R^5$ and $R^6$ are as defined herein except that $R^3$ and $R^4$ may not be hydrogen when X is NH, and L is a leaving group:

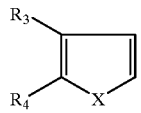

(II)

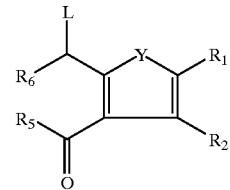

(III)

Preferred catalysts are Montmorillonite $K_{10}$ clay or p-toluenesulphonic acid. Preferred solvents are 1,2-dichloroethane or toluene. Examples of suitable leaving groups include —$OCOCH_3$, OEt, —$N^+Me_3$ and halo.

Insertion of the substituent $R^1$ onto the ring system for example:

(d) Carboxylation of a polyheterocyclic compound using
  (i) a carbonyl halide or
  (ii) carbon dioxide According to known procedures (J. March, Advanced Organic Chemistry, 2nd ed, McGraw Hill, New York, 1977, p 497–498).

(e) Alternatively one can produce compounds of the formula (I) wherein $R^2$ is CHO by methods known to those skilled in the art, for example:

(i) The appropriate aromatic polyheterocycle can be reacted with a formylating agent, such as that generated by the reaction between $SnCl_4$ and $Cl_2CHOCH_3$ or equivalent reagents.

For example, according to the method of A. Reiche et al, Chem. Ber. 93, 88 (1960), or with other standard formylating reagents/procedures known in the art, for example, the Gatterman-Koch reaction (CO\HCl\AlCl$_3$\CuCl), the Gatterman reaction (HCN\HCl\ZnCl$_2$), and the Vilsmeier reaction (POCl$_3$\PhN—(Me)CHO or POCl$_3$\Me$_2$CHO) (J. March, Vide Supra, p 494–497); or (ii) the appropriate aromatic polyheterocycle, carrying a suitable functional group, said group being converted to an aldehyde group by methods known to those skilled in the art. Suitable functional groups include $CHBr_2$, $CH_3$, $COR^{14}$ wherein $R^{14}$ is a primary or secondary $C_{1-6}$ alkyl group, COOH or a derivative thereof such as an ester, amide, acid chloride or CN; or (f) Compounds of the formula (I) wherein $R^1$ is $CONHR^{10}$ may also be produced by the reaction of a compound wherein $R^1$ is COOH or a suitable reactive acid derivative thereof as outlined in J. March, Vide supra. For example an acid halide can be reacted with a compound $NH_2R^{10}$ in an inert solvent.

(g) Conversion of one compound of formula (I) into another compound of formula (I).

Compounds of the invention wherein $R^1$ is $COOR^8$ and $R^8$ is, for example, aralkyl can be converted to free acids wherein $R^8$ is H by reduction in the presence of $H_2$ and a Pd catalyst, or where $R^8$ is, for example, alkyl, by hydrolysis in the presence of an appropriate base e.g. caesium carbonate.

It is thereafter possible for the skilled man to synthesize ester and amide compounds within the scope of the invention by conversion of the free acids obtained, by known procedures. (See J. March, Vide Supra, p363–365).

Compounds of the invention produced as described herein can be converted to other compounds of the invention by electrophilic substitution at $R^5$ and/or $R^6$, to introduce, for example, $NO_2$, halogen and $COR^{13}$ wherein $R^{13}$ is as defined herein.

Compounds of formula I in which X or Y is $NR_7$ and $R_7$ is COOMe can be converted by acid or base hydrolysis to compounds of formula I in which X or Y are NH using, for example, potassium hydroxide or HBr in acetic acid.

The above processes have been described for compounds wherein A is

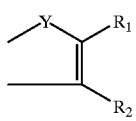

The skilled person will appreciate that these are equally applicable when A is

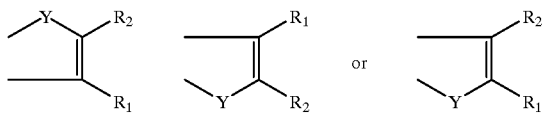

The compounds of the present invention are useful for the treatment of tumours. They may be employed in treating various forms of cancer of mammals including carcinomas, for instance of the stomach, pancreas, breast, uterus and colon; adenocarcinomas, for instance of the lung and colon; sarcomas, for instance fibrosarcoma; leukaemias, for instance lymphocytic leukaemia and lymphomas, for instance myeloid lymphoma.

The invention thus further provides a method for the treatment of tumours in animals, including mammals, especially humans, which comprises the administration of a clinically useful amount of compound of formula (I) or a pharmaceutically acceptable salt or physiologically functional derivative in a pharmaceutically useful form, once or several times a day or in any other appropriate schedule, orally, rectally, parenterally, or applied topically.

In addition, there is provided as a further, or alternative, aspect of the invention, a compound of formula (I) or a pharmaceutically acceptable salt or physiologically functional derivative thereof for use in therapy, for example as an antitumour agent.

The amount of compound of formula (I) required to be effective against the aforementioned tumours will, of course, vary and is ultimately at the discretion of the medical or veterinary practitioner. The factors to be considered include the condition being treated, the route of administration, and nature of the formulation, the mammal's body weight, surface area, age and general condition, and the particular compound to be administered. A suitable effective antitumour dose is in the range of about 0.01 to about 100 mg/kg body weight, eg 0.1 to about 100 mg/kg body weight, preferably 1–30 mg/kg body weight. The total daily dose may be given as a single dose, multiple doses, e.g., two to six times per day or by intravenous infusion for selected duration. For example, for a 75 kg mammal, the dose range would be about 8 to 900 mg per day, and a typical dose could be about 50 mg per day. If discrete multiple doses are indicated treatment might typically be 15 mg of a compound of formula (I) given up to 4 times per day.

Whilst it is possible for the active compound to be administered alone, it is preferable to present the active compound in a pharmaceutical formulation. Formulations of the present invention, for medical use, comprise a compound of formula (I) or a salt thereof together with one or more pharmaceutically acceptable carriers and optionally other therapeutic ingredients. The carrier(s) should be pharmaceutically acceptable in the sense of being compatible with the other ingredients of the formulation and not deleterious to the recipient thereof.

The present invention, therefore, further provides a pharmaceutical formulation comprising a compound of the formula (I) or a pharmaceutically acceptable salt or physiologically functional derivative thereof together with a pharmaceutically acceptable carrier thereof.

There is also provided a method for the preparation of a pharmaceutical formulation comprising bringing into association a compound of formula (I) or a pharmaceutically acceptable salt or physiologically functional derivative thereof, and a pharmaceutically acceptable carrier thereof.

Formulations according to the present invention include those suitable for oral, topical, rectal or parenteral (including subcutaneous, intramuscular and intravenous) administration. Preferred formulations are those suitable for oral or parenteral administration.

The formulations may conveniently be presented in unit dosage form and may be prepared by any of the methods well known in the art of pharmacy. All methods include the step of bringing the active compound into association with a carrier which constitutes one or more accessory ingredients. In general, the formulations are prepared by uniformly and intimately bringing the active compound into association with a liquid carrier or a finely divided solid carrier or both and then, if necessary, shaping the product into desired formulations.

Formulations of the present invention suitable for oral administration may be presented as discrete units such as capsules, cachets, tablets or lozenges, each containing a predetermined amount of the active compound; as a powder or granules; or a solution or suspension in an aqueous or non-aqueous liquid such as a syrup, an elixir, an emulsion or a draught.

A tablet may be made by compression or moulding, optionally with one or more accessory ingredients. Compressed tablets may be prepared by compressing in a suitable machine the active compound in a free-flowing form such as a powder or granules, optionally mixed with a binder, lubricant, inert diluent, surface active or dispersing agent. Moulded tablets may be made by moulding in a suitable machine a mixture of the powdered active compound with any suitable carrier.

A syrup may be made by adding the active compound to a concentrated, aqueous solution of a sugar, for example sucrose, to which may also be added any accessory ingredients. Such accessory ingredient(s) may include flavourings, an agent to retard crystallization of the sugar or an agent to increase the solubility of any other ingredients, such as a polyhydric alcohol for example glycerol or sorbitol.

Formulations for rectal administration may be presented as a suppository with a conventional carrier such as cocoa butter.

Formulations suitable for parenteral administration conveniently comprise a sterile aqueous preparation of the active compound which is preferably isotonic with the blood of the recipient. Such formulations suitably comprise a solution of a pharmaceutically and pharmacologically acceptable acid addition salt of a compound of the formula (I) that is isotonic with the blood of the recipient.

Useful formulations also comprise concentrated solutions or solids containing the compound of formula (I) which upon dilution with an appropriate solvent give a solution for parenteral administration as above.

In addition to the aforementioned ingredients, the formulations of this invention may further include one or more accessory ingredient(s) selected from diluents, buffers, flavouring agents, binders, surface active agents, thickeners, lubricants, preservatives (including antioxidants) and the like.

In a further aspect the present invention provides the use of a compound of formula (I) or a pharmaceutically acceptable salt or physiologically functional derivative thereof for the manufacture of a medicament for the treatment of tumours.

The invention will now be illustrated by the following non-limiting Examples:

All temperatures are in degrees Celsius (°C.)

IR spectra were recorded on a Perkin-Elmer 257 grating spectrophotometer or a Bruker FS66 spectrophotometer.

U.V. spectra were measured in ethanol on a Unicam SP800 spectrophotometer.

1H NMR spectra were obtained on a Bruker WM 360-NMR spectrophotometer at 360 MHz, or on a Bruker AC200 spectrophotometer at 200 MHz. J values are given in Hz.

Mass spectra were obtained on Varian CH5D(EI), Kratos Concept (EI) or Kratos Ms50(FAB) instruments.

EXAMPLE 1

Diethyl 1,5-dihydro-3,4,6-trimethylpyrrolo[2,3-f] indole-2,7-dicarboxylate

A solution of ethyl 5-acetoxymethyl-4-acetyl-3-methylpyrrole-2-carboxylate (0.267 g, 1.0 mmol) and 3-carbethoxy-2-methylpyrrole (0.153 g, 1.0 mmol) in 1,2-dichloroethane (10 cm$^3$) was heated at reflux and stirred with Montmorillonite clay (1 g) for 18 h. After filtration from clay and washing well with 1,2-dichloroethane, evaporation of the combined filtrates under reduced pressure gave an oil. This oil was submitted to flash chromatography on silica eluting with (0–20%) ethyl acetate in dichloromethane to give the starting 3-carbethoxy-2-methylpyrrole (0.045 g, 29.4%) and diethyl 1,5-dihydro-3,4,6-trimethylpyrrolo[2,3-f]indole-2,7-dicarboxylate as a colourless solid (0.021 g, 6.14%) m.p. 269° C. (decomp); δH ([$^2$H$_6$]-DMSO)11.34 (1H, s, 5-NH), 11.00 (1H, s, 1-NH), 7.80 (1H, s, 8-H), 4.33 (2H, q, 7-OCH$_2$CH$_3$), 4.26 (2H, q, 2-OCH$_2$CH$_3$), 2.85 (6H, s, 3-CH$_3$ and 4-CH$_3$), 2.69 (3H, s, 6-CH$_3$), 1.39 (3H, t, 7-OCH$_2$CH$_3$), and 1.37 (3H, t, 2-OCH$_2$CH$_3$); saturation of the singlet 8-H at δ 7.80 enhanced the signal due to 1-NH at δ 11.00 (2.3%); m/z (%) 342 (75,M$^+$), 296 (100), 268 (6), 223 (7) and 195 (5) (Found: M$^+$ 342.1580. C$_{19}$H$_{22}$N$_2$O$_4$ requires M, 342.1579; λ max EtOH/nm (log ε max.dm$^3$ mol$^{-1}$ cm$^{-1}$ 378 (3.56), 365 sh (353), 329 (3.83), 3.04 (3.99) and 259 (3.74). Further elution gave diethyl 1,7-dihydro-3,4,6-trimethylpyrrolo[3,2-f]indole-2,5-dicarboxylate as a colourless solid (0.048 g, 14%) m.p. 216–216.5° C. (Found: C, 66.82; H, 6.68; N, 8.17. C$_{19}$H$_{22}$N$_2$O$_4$ requires C, 66.65; H, 6.48, N, 8.18%); δ ([$^2$H$_6$]-DMSO) 11.30 (1H, s, 7-NH), 10.91 (1H, s, 1N-H), 7.12 (1H, s, 8–11), 4.35 (2H, q, 5-OCH$_2$CH$_3$), 4.28 (2H, q, 2-OCH$_2$CH$_3$), 2.90 (3H, s, 4-CH$_3$), 2.87 (3H, s, 3-CH$_3$, 2.54 (3H, s, 6-CH$_3$), 1.36 (3H, t, 5-OCH$_2$CH$_3$) and 1.34 (3H, t, 2-OCH$_2$CH$_3$); saturation of the 8-H proton at δ 7.12 enhanced the signals due to 7-NH at δ 11.30 (2.4%) and 1-NH at δ 10.91 (1.8%); m/z (%) 342 (64, M$^+$), 296 (100), 250(5), and 194(9); λ max (EtOH)/nm (log ε max/dm$^3$ mol$^{-1}$ cm$^{-1}$) 340 (4.10), 327.5 (4.53) and 270 (4.46), and the starting 5-acetoxymethyl-4-acetylpyrrole (0.029 g, 10.9%).

EXAMPLE 2

Ethyl 1,7-dihydro-3,4,6-trimethylpyrrolo[3,2-f] indole-2-carboxylate

The general procedure of Example 1 was followed using ethyl 5-acetoxymethyl-4-acetyl-3-methylpyrrolo-2 carboxylate (0.692 g, 2.59 mmol), 3-methoxycarbonyl-2-methylpyrrole (0.360 g, 2.59 mmol), 1,2-dichloroethane (25 cm$^3$) and Montmorillonite clay (2 g). Chromatographic separation using (0–20%) ethyl acetate in dichloromethane gave ethyl 1,7-dihydro-3,4,6-trimethylpyrrolo[3,2-f]indole-2-carboxylate as a pale yellow solid (0.0124 g, 1.8%) m.p. 213–216° C. (decomp); δH ([$^2$H$_6$]-DMSO) 10.70 (1H, s, 1-NH), 10.41 (1H, s, 7-NH), 7.03 (1H, s 8-H), 6.14 (1H, s, 5-H), 4.33 (2H, q, CH$_2$CH$_3$), 2.85 (3H, s, 3-CH$_3$), 2.78 (3H, s, 4-CH$_3$), 2.37 (3H, s, 6-CH$_3$), and 1.35 (3H, s, OCH$_2$CH$_3$); saturation of the 8-H proton at δ 7.03 enhanced the signals due to 1-NH at δ 10.70 (3.5%) and 7-NH at δ 10.41 (2.9%) and saturation of the 5-H proton at δ 6.14 enhanced the signals due to 4-CH$_3$ at 2.78 (2%) and 6-CH$_3$ at 2.37 (0.6%); m/z (%) 270 (M$^+$, 49), 234 (100), 196 (17) (Found: M$^+$270.1337. C$_{16}$H$_{18}$N$_2$O$_2$ requires M 270.368, and the starting 3-methoxycarbonyl-2-methylpyrrole (0.108 g, 30%). Further elution gave ethyl methyl 1,7-dihydro-3,4,6-trimethylpyrrolo[3,2-f]indole-2,5-dicarboxylate as a colourless solid (0.066 g, 7.8%) m.p. 247–250° C. (Found: C, 66.11; H, 6.37; N, 8.47. C$_{18}$H$_{20}$N$_2$O$_4$ requires C, 65.84; H, 6.14; N, 8.53); δH ([$^2$H$_6$]-DMSO) 11.33 (1H, s, 7-NH), 10.91 (1H, s, 1-NH), 7.21 (1H, s, 8-H), 4.35 (2H, q, OCH$_2$CH$_3$], 3.78 (3H, s, OCH$_3$), 2.88 (3H, s, CH$_3$), 2.87 (3H, s, CH$_3$), 2.53 (concealed by DMSO, 6-CH$_3$) and 1.37 (3H, t, OCH$_2$CH$_3$); m/z (%) 328 (64, M$^+$), 297 (5), 282 (100), 250 (6), 221 (6) and 194 (17) and the starting 5-acetoxymethyl-4-acetylpyrrole (0.037 g, 5.4%).

EXAMPLE 3

Ethyl 6-Benzyloxycarbonyl-3,4-dimethylpyrrolo[3,2-f]indole-2-carboxylate (a) Reaction of benzyl pyrrole-2-carboxylate and ethyl 5-acetoxymethyl-4-acetyl-3-methylpyrrole-2-carboxylate A solution of benzyl pyrrole-2-carboxylate (0.615 g, 3.06 mmol) and ethyl 5-acetoxymethyl-4-acetyl-3-methylpyrrole-2-carboxylate (0.809, 3.01 mmol) in 1,2-dichloroethane (30 cm$^3$) was heated under reflux and stirred with Montmorillonite clay (3 g) for 7 h. The reaction was followed to completion by TLC. After the clay had been filtered off and washed well with 1,2-dichlorethane, evaporation of the combined filtrates under reduced pressure gave a yellow oil. This was submitted to column chromatography eluting with (5–50%) ethyl acetate in n-hexane to give the starting pyrrole, benzylpyrrole-2-carboxylate (0.153 g, 24.80%) Ethyl 6-Benzyloxycarbonyl-3,4-dimethylpyrrolo [2,3-f]indole-2-carboxylate (isomer I) as a yellow solid (0.043 g, 3.67%), m.p. 218–220° C. (Found: C, 70.90; H, 5.87; N, 7.34. C$_{23}$H$_{22}$N$_2$O$_4$ requires C, 70.75; H, 5.68; N, 7.18%); δH ([$^2$H$_6$]-DMSO) 11.18 (1H, br s, 5-NH), 10.97 (1H, br s, 1-NH), 7.52 (2H, d J 7, O-H's of ArH), 7.36–7.48 (3H, m, m and p H's of ArH), 7.46 (1H, s, 8-H), 7.23 (1H, d J 1.5, 7-H), 5.41 (2H, s, OCH$_2$Ph), 4.35 (2H, q, OCH$_2$CH$_3$), 2.93 (3H, s, 4-CH$_3$), 2.85 (3H, s, 3-CH$_3$) and 1.38 (3H, t, OCH$_2$, CH$_3$); m/z (%) 390 (100, M$^+$), 344 (71), 282 (59), 236 (60), 228 (27), 209 (21) and 91 (78); V max (nujol) 3400, 3350, 1725 and 1680 cm$^{-1}$; and Ethyl 6-Benzyloxycarbonyl-3,4-dimethylpyrrolo[3,2-f]indole-2-carboxylate (isomer II) as a yellow solid (0.065 g, 5.55%), m.p. 179–182° C., δH ([$^2$H$_6$]-DMSO) 11.36 (1H, br s, 7-NH), 10.95 (1H, br s, 1-NH), 7.52 (2H, d J 7, O-H's of ArH), 7.48–7.37 (3H, m, m and p H's of ArH), 7.34 (1H, br s, 5-H), 7.19 (1H, br s, 8-H), 5.39 (2H, s, CH$_2$Ph), 4.35 (2H, q, OCH$_2$CH$_3$), 2.89 (3H, s, 4-CH$_3$), 2.84 (3H, s, 3-CH$_3$) and 1.37 (OCH$_2$, CH$_3$); m/z (%) 390 (4, M$^+$), 344 (7), 306 (5), 282 (5), 236 (6), 209 (15), 154 (18), 127 (19) and 91 (100) (Found: M$^+$ 390.1580. C$_{23}$H$_{22}$N$_2$O$_4$ requires 390.1579).

Also obtained were 2-(3'-acetyl-5'-ethoxycarbonyl-4'-methylpyrrol-2'-ylmethyl)-5-benzoxycarbonylpyrrole as off-white crystals after crystallization from dichloromethane-petroleum ether (0.303 g, 24.75%), m.p. 130–132° C., δH ([$^2$H$_6$]-DMSO) 11.96 (1H, s, 1-NH), 11.65 (1H, s, 1'-NH), 7.45–2.31 (5H, m, ArH), 6.70 (1H, t J2.6, 4-H), 5.75 (1H, dd J 2.6 and 4, 3-H), 5.27 (2H, S, CH$_2$Ph), 4.28 (2H, q, OCH$_2$CH$_3$), 4.20 (2H, s, CH$_2$), 2.50 (concealed by DMSO, 4'-CH$_3$), 2.34 (3H, s, COCH$_3$) and 1.31 (3H, t, OCH$_2$CH$_3$); saturation of the 4-H at δ 6.70 enhanced the signal due to 3-H double doublet at δ 5.75 (6%) and saturation of the singlet CH$_2$ at δ 4.20 enhanced the signals due to 3-H at δ 5.75 (4.5%), 1-NH at δ 11.96 (4.5%) and 1'-NH at δ 11.65 (4.5%); m/z (%) 408 (14, M$^+$), 317 (100), 271 (97), 91 (47) (Found: M$^+$NH$_4^+$426.2029. C$_{23}$H$_{24}$N$_2$O$_5$+ NH$_4^+$ requires 426.2028) and 2,3-di(3'-acetyl-5'-ethoxycarbonyl-4'-methyl-2'-ylmethyl)-5-benzoxycarbonylpyrrole as colourless crystals after crystallization from benzene-petroleum ether (0.256 g, 27.75%), m.p. 164–166° C. (Found: C, 66.53; H, 6.24; N, 6.71. C$_{34}$H$_{37}$N$_3$O$_8$ requires C, 66.33; H, 6.06; N, 6.83%); δH (CDCl$_3$), 10.50 (1H, br s, 1-NH), 9.10 (2H, br s, 2X NH), 7.42–7.20 (5H, m, ArH), 6.65 (1H, d J 2.5, 4-H), 5.23 (2H, s, CH$_2$Ph), 4.32 (2H, q, 2-OCH$_2$CH$_3$), 4.30 (2H, q, 3-OCH$_2$CH$_3$), 4.13 (2H, s, 2-CH$_2$), 4.08 (2H, s, 3-CH$_2$), 2.60 (3H, s, CH$_3$), 2.59 (3H, s, CH$_3$), 2.55 (3H, s, COCH$_3$), 2.54 (3H, s, COCH$_3$), 1.36 (3H, t, 2-OCH$_2$CH$_3$) and 1.35 (3H, t, 3-OCH$_2$CH$_3$).

(b) Cyclisation of 2-(3'-acetyl-5'-ethoxycarbonyl-4'-methylpyrrol-2'-ylmethyl-5-benzoxycarbonylpyrrole A solution of the 2-pyrrolylmethylpyrrole (0.083 g), 0.2 mmol) in 1,2-dichloroethane (5 ml) was heated under reflux and stirred with Montmorillonite clay (0.25 g) for 14 h. The reaction was followed by TLC. After the clay has been filtered off and washed well with 1,2-dichloroethane, evaporation of the combined filtrates under reduced pressure gave an oil. Chromatagraphic separation of an oil eluting with (5–30%) ethyl acetate in hexane yielded Ethyl 6-Benzyloxycarbonyl-3,4-dimethylpyrrolo[2,3-f]indole-2-carboxylate (isomer I) as a yellow solid (0.0047 g, 6%) which was identical to isomer I obtained from (a) by TLC and nmr; and Ethyl 6-Benzyloxycarbonyl-3,4-dimethylpyrrolo[3,2-f]indole-2-carboxylate (isomer II) as a yellow solid (0.0285 g, 36%) which was identical to isomer II obtained from (a) by TLC and NMR; and the starting 2-pyrrolylmethylpyrrole (0.0116 g, 14%).

EXAMPLE 4

Dibenzyl 3,4-dimethylpyrrolo[3,2-f]indole-2,6-dicarboxylate

A solution of benzyl pyrrole-2-carboxylate (0.201 g, 1.0 mmol) and benzyl 5-acetoxymethyl-4-acetyl-3-methylpyrrole-2-carboxylate (0.331 g, 1.0 mmol) in 1,2-dichloromethane (10 cm$^3$) was heated under reflux and stirred with Montmorillonite clay (1 g) for 7 h. The reaction was followed to completion by TLC. After the clay had been filtered off and washed well with 1,2-dichloroethane, evaporation of the combined filtrates under reduced pressure gave an oil. This was submitted to column chromatography eluting with (5–50%) ethyl acetate in hexane to give Dibenzyl 3,4-dimethylpyrrolo[2,3-f]indole-2,6-dicarboxylate (isomer I) as yellow crystals after crystallization from ethyl acetate-petroleum ether (0.019 g, 4.20%), m.p. 210–212° C. (Found: C, 73.50; H, 5.29; N, 6.13. C$_{28}$H$_{24}$N$_2$O$_4$ requires C, 73.62; H, 5.49; N, 6.36%); δH ([$^2$H$_6$]-DMSO) 11.17 (1H, s, 5-NH), 11.02 (1H, s, 1-NH), 7.57–7.34 (11H, m, 2×ArH and 8-H), 7.23 (1H, d J 1.5, 7-H), 5.42 (2H, s, CH$_2$Ph), 5.40 (2H, s, CH$_2$Ph), 2.93 (3H, s, 4-CH$_3$), 2.87 (3H, s, 3-CH$_3$); m/z (%) 452 (68, M$^+$), 344 (58), 236 (17), and 91 (100); and Dibenzyl 3,4-dimethylpyrrolo[3,2-f]indole-2,6-dicarboxylate (isomer II) as yellow crystals after crystallization from dichloromethane-petroleum ether (0.036 g, 7.96%), m.p. 184–186° C. (Found: C, 73.71; H, 5.59; N, 6.27. C$_{28}$H$_{24}$N$_2$O$_4$ requires C, 73.62; H, 5.49; N, 6.36%); δH ([$^2$H$_6$]-DMSO) 11.36 (1H, s, 7-NH), 10.99 (1H, s, 1-NH), 7.52 (4H, d J 7, O-ArH), 7.46–7.37 (7H, m, m and p-ArH and 8-H), 7.23 (1H, br s, 5-H), 5.40 (4H, s, 2× CH$_2$Ph), 2.91 (3H, s, 3-CH$_3$) and 2.86 (3H, s, 4-CH$_3$); m/z (%) 452 (55, M$^+$), 344 (59), 236 (10), and 91 (100). Further elution gave 2-(3'-acetyl-5'-benzoxycarbonyl-4-methylpyrrol-2'-ylmethyl)-5-benzoxycarbonylpyrrole as pale yellow crystals after crystallization from dichloromethane-petroleum ether (0.104 g, 22.13%), m.p. 141–143° C. (Found: C, 71.60; H, 5.59; N, 5.79. C$_{28}$H$_{26}$N$_2$O$_5$ requires C, 71.47; H, 5.57; N, 5.95%); δH (CDCl$_3$) 10.22 (1H, s, 1-NH), 9.25 (1H, s, 1'-NH), 7.48–7.28 (10H, m, ArH), 6.83 (1H, dd J 2.5 and 4, 4-H), 6.05 (1H, dd J 2.5 and 4, 3-H), 5.28 (2H, s, CH$_2$Ph), 5.26 (2H, s, CH$_2$Ph), 4.13 (2H, s, CH$_2$), 2.58 (3H, s, CH$_3$, 2.49 (3H, s, COCH$_3$); m/z (%) 470 (6, M$^+$), 379 (45), 271 (32), 91 (100), 65 (61) and 43 (38) and 2,3-di(3'-acetyl-5'benzoyxcarbonyl-4'-methylpyrrole-2'-ylmethyl)-5-benzoxycarbonylpyrrole as an oil (0.0924 g, 25.01%); δH (CDCl$_3$) 11.18 (1H, s, 1-NH), 10.46 (1H, s, NH), 9.31 (1H, s, NH), 7.42–7.27 (15H, m ArH), 6.61 (1H, d J 2, 4-H), 5.31 (2H, s, CH$_2$Ph), 5.29 (2H, s, CH$_2$ Ph), 5.22 (2H, s, CH$_2$Ph), 4.13 (2H, s, 2-CH$_2$), 4.05 (2H, s, 3-CH$_2$), 2.57 (3H, s, CH$_3$), 2.55 (3H, s, CH$_3$), 2.51 (3H, s, CH$_3$), 2.37 (3H, s, CH$_3$); m/z (%) 739 (2, M$^+$), 696 (20), 648 (27), 631 (20), 588 (95). (Found: M$^+$739.2890. C$_{44}$H$_{41}$N$_3$O$_8$ requires 730.2893)

EXAMPLE 5

Ethyl6-methoxycarbonyl-3,4-dimethylpyrrolo[3,2-f] indole-2-carboxylate

A solution of methyl pyrrole-2-carboxylate (0.222 g, 1.7 mmol) and ethyl 5-acetoxymethyl-4-acetyl-3-methylpyrrole-2-carboxylate (0.474 g, 1.7 mmol) in 1,2-dichloroethane (20 cm$^3$) was heated under reflux and stirred with Montmorillonite clay for 7 h. The reaction was followed to completion by TLC. After the clay had been filtered off and washed well with 1,2-dichloroethane, evaporation of the combined filtrates under reduced pressure gave an oil. Chromatographic separation of an oil eluting with (5–40%) ethylacetate in hexane gave Ethyl 6-methoxycarbonyl-3,4-dimethylpyrrolo[2,3-f]indole-2-carboxylate (isomer I) as a yellow solid after crystallisation from dichloromethane-petroleum ether (0.030 g, 5.62%), m.p. 245–248° C.; δH ([$^2$H$_6$]-DMSO) 11.16 (1H, s, 5-NH), 11.00 (1H, s, 1-NH), 7.45 (1H, s, 8-H), 7.20 (1H, s 7-H), 4.37 (2H, q, OCH$_2$CH$_3$), 3.91 (3H, s, OCH$_3$), 2.95 (3H, s, 3-CH$_3$), 2.88 (3H, s, 4-CH$_3$), 1.37 (3H, t, OCH$_2$CH$_3$); saturation of the 1-NH at δ 11.00 enhanced the signal due to 8-H at δ 7.45 (3.9%), saturation of the 4-CH$_3$ of δ 2.88 enhanced the signal due to 5-NH at δ 11.16 (12.3%) and saturatoin of the 5-NH at 11.16 enhanced the signal due to 4-CH$_3$ at δ 2.88 (2%); m/z (%) 314 (81, M$^+$), 282 (55), 268 (89), 236 (100), 208 (56), 179 (50), 153 (48), 118 (56), 90 (82) and 77 (72) (Found: M$^+$314.1267. C$_{17}$H$_{18}$N$_2$O$_4$ requires 314.1266; Ethyl 6-methoxycarbonyl-3,4-dimethylpyrrolo[3,2-f]indole-2-carboxylate (isomer II) as yellow crystals after crystallization from dichloromethane-petroleum ether (0.0584 g, 10.94%), m.p. 242–245° C.; δH ([$^2$H$_6$]-DMSO) 11.36 (1H, s, 7-NH), 10.92 (1H, s, 1-NH), 7.33 (1H, s, 8-H), 7.24 (1H, s 5-H), 4.36 (2H, q, OCH$_2$CH$_3$), 3.89 (3H, s, OCH$_3$), 2.92 (3H, s, 3-CH$_3$), 2.87 (3H, s, 4-CH$_3$), 1.37 (3H, t, OCH$_2$CH$_3$); m/z (%) 314 (60, M$^+$), 282 (50), 268 (62), 236 (60), 208 (60), 179 (55), 165 (34), 152 (52), 134 (48), 127 (56) and 188 (100) (Found: M$^+$314.1267. C$_{17}$H$_{18}$N$_2$O$_4$ requires 314.1266); Further elution gave 2-(3'-acetyl-5'-ethoxycarbonyl-4'-methylpyrrol-2-ylmethyl-5-methoxycarbonylpyrrole as off-white crystals after crystallization from dichloromethane-petroleum ether (0.0912 g, 16.16%), m.p. 160–162° C.; δH (CDCl$_3$), 10.40 (1H, s, 1-NH), 9.78 (1H, s, 1'-NH), 6.79 (1H, dd J 4 and 2.5, 4-H), 6.09 (1H, dd J 4 and 2.5, 3-H), 4.30 (2H, q, OCH$_2$CH$_3$); 4.22 (2H, s, CH$_2$), 3.80 (3H, s, OCH$_3$), 2.58 (3H, s, CH$_3$), 2.50 (3H, s COCH$_3$), 1.33 (3H, t, OCH$_2$CH$_3$; m/z (%) 332 (66, M$^+$), 300 (55), 271 (54), 254 (66), 227 (61), 211 (55), 183 (65), 155 (59), 128 (66), 106 (85), 94 (45), 78 (66), 51 (37), 43 (100); and 2,3-di(3-acetyl-5-ethoxycarbonyl-4-methylpyrrol-2'-ylmethyl-5-methoxycarbonylpyrrole as off-white crystals after crystallization from benzene-petroleum ether (0.1885 g, 41.15%), m.p. 203–206° C. (Found: C, 62.24; H, 6.16; N, 7.66. C$_{28}$H$_{33}$N$_3$O$_8$ requires, C, 62.32; H, 6.16; N, 7.79%); δH (CDCl$_3$) 11.08 (1H, s, NH), 9.42 (1H, s, NH), 9.13 (1H, s, NH), 6.63 (1H, d J 2, 4-H), 4.33 (2H, q, OCH$_2$CH$_3$); 4.32 (2H, q, OCH$_2$CH$_3$), 4.13 (2H, s, 2-CH$_2$), 4.11 (2H, s, 3-CH$_2$), 3.77 (3H, s, OCH$_3$), 2.61 (3H, s, CH$_3$), 2.59 (3H, s, CH$_3$), 2.57 (6H, s, 2×CH$_3$), 1.37 (3H, t, OCH$_2$CH$_3$), 1.36 (3H, t, OCH$_2$CH$_3$).

EXAMPLE 6

Ethyl 7-Methoxycarbonyl-3,4-Dimethylpyrrolo[3,2-f]indole-2-Carboxylate (a) Reaction of 1-methyloxycarbonylpyrrole and ethyl 5-acetoxy-methyl-4-acetyl-3-methylpyrrole-2-carboxylate A solution of 1-methoxycarbonylpyrrole (1.000 g, 8 mmol) and ethyl 5-acetoxymethyl-4-acetyle-3-methyl-2-carboxylate (2.136 g, 8 mmol) in 1,2-dichloroethane (80 cm$^3$) was heated under reflux and stirred with Montmorillonite clay (8 g) for 18 h. After the clay had been filtered off and washed well with 1,2-dichloroethane, evaporation of the combined filtrates under reduced pressure gave an oil. This was submitted to column chromatography eluting with (20–0%) petroleum ether in dichloromethane and (0–25%) ethyl acetate in dichloromethane to give the starting 1-methoxycarbonylpyrrole (0.1448 g, 14.48%); 3-chloro-5-ethoxycarbonyl-2-(1'-methoxycarbonylpyrrol-2'-ylmethyl)-4-methylpyrrole as colourless crystals after crystallization from benzene-petroleum ether (0.0143 g, 5.51%) m.p. 144–145° C. (Found: C, 55.27; H, 5.45; N, 8.43. C$_{15}$H$_{17}$N$_2$O$_4$Cl requires C, 55.47; H, 5.28; N, 8.63%); δH (CDCl$_3$) 9.23 (1H, br s, NH), 7.20 (1H, t, J 2.5, 4'-H), 6.12 (2H, d J 2.5, 3'- and 5'-H), 4.29 (2H, q, OCH$_2$CH$_3$), 4.21 (2H, s, CH$_2$), 3.97 (3H, s, OCH$_3$), 2.26 (3H, s, CH$_3$), 1.34 (3H, t, OCH$_2$CH$_3$); m/z (%) 326 (10, M$^+$-2), 324 (28, M$^+$), 297 (7), 295 (22), 289 (88), 279 (23), 277 (37); 243 (86), 221 (24), 219 (66), 185 (45), 155 (75), 142 (21), 128 (32), 101 (30), 90 (30), 80 (75), 67 (70), 59 (100). Ethyl 5-methoxycarbonyl-3,4-dimethylpyrrolo[2,3-f]indole-2-carboxylate (isomer I) as colourless crystals after crystallization from dichloromethane-petroleum ether (0.0263 g, 1.05%) m.p. 163–165° C. (Found: C, 64.73; H, 5.79; N, 8.77. C$_{17}$H$_{18}$N$_2$O$_4$ requires C, 64.95; H, 5.77; N, 8.91%); δH ([$^2$H$_6$]-DMSO) 11.33 (1H, s, NH), 7.64 (1H, d J 3.5, 6-H), 7.38 (1H, s, 8-H), 6.72 (1H, d J 3.5, 7-H), 4.35 (2H, q, OCH$_2$CH$_3$), 3.95 (3H, s, OCH$_3$), 2.86 (3H, s, 3-CH$_3$), 2.75 (3H, s, 4-CH$_3$) and 1.37 (3H, t, OCH$_2$CH$_3$); m/z (%) 314 (57, M$^+$), 268 (100), 240 (18), 209 (19), 195 (25), 181 (52), 154 (42), 127 (28), 77 (26) and 59 (82); and Ethyl 7-methoxycarbonyl-3,4-dimethylpyrrolo[3,2-f]indole-2-carboxylate (isomer II) as colourless solid (0.6027 g, 23.99%) m.p. 197–200° C. (Found: C, 64.82; H, 5.55; N, 8.74. C$_{17}$H$_{18}$N$_2$O$_4$ requires C, 64.92; H, 5.77; N, 8.91%) δH ([$^2$H$_6$]-DMSO) 11.37 (1H, s, NH), 8.03 (1H, s, 8-H), 7.58 (1H, d j 3.5, 6-H), 6.88 (1H, d J3.5, 5-H), 4.35 (2H, q, OCH$_2$CH$_3$), 3.99 (3H, s, OCH$_3$), 2.86 (6H, s 2×CH$_3$), 1.36 (3H, t, OCH$_2$CH$_3$); m/z (%) 314 (53, M$^+$), 268 (100), 240 (13), 209 (21), 195 (12), 181 (12), 154 (13) and 127 (16). Further elution gave 3-acetyl-5-ethoxycarbonyl-2-(1'-methoxycarbonylpyrrol-2'-ylmthyl)-4-methylpyrrole as colourless solid (0.1588 g, 5.98%) m.p. 172–175° C. (FoundL C, 61.38; H, 6.22; N, 8.40. C$_{17}$H$_{20}$N$_2$O$_5$ requires C, 61.43; H, 6.07; N, 8.43%); δH (CDCl$_3$) 9.53 (1H, br s, NH), 7.21 (1H, dd J 3.5 and 2, 5'-H), 6.26 (1H, m, 4'-H), 6.13 (1H, t J 3.5, 3-H), 4.56 (2H, s, CH$_2$), 4.31 (2H, g, OCH$_2$CH$_3$), 3.95 (3H, s, OCH$_3$), 2.59 (3H, s, 4-CH$_3$), 2.47 (3H, s COCH$_3$), and 1.35 (3H, t, OCH$_2$CH$_3$); m/z (%) 332 (28, M$^+$), 289 (92), 243 (100), 227 (22), 185 (28), 155 (16), 130 (10), 77 (24), 59 (35), 43 (90); 6-(3'-acetyl-5'-ethoxycarbonyl-4'-methylpyrrol-2'-ylmethyl)-2-ethoxycarbonyl-7-methoxycarbonyl-3,4-dimethylbenzo[1,2-b: 5,4-b']dipyrrole as off-white solid (0.1593 g, 7.64%) Ethyl 5-methoxycarbonyl-3,4-dimethylpyrrolo[2,3-f] indole-2-carboxylate (isomer I) as colourless crystals after crystallization from dichloromethane-petroleum ether (0.0263 g, 1.05%) m.p. 163–165° C. (Found: C, 64.73; H, 5.79; N, 8.77. C$_{17}$H$_{18}$N$_2$O$_4$ requires C, 64.95; H, 5.77; N, 8.91%); δH ([$^2$H$_6$]-DMSO) 11.33 (1H, s, NH), 7.64 (1H, d J 3.5, 6-H), 7.38 (1H, s, 8-H), 6.72 (1H, d J 3.5, 7-H), 4.35 (2H, q, OCH$_2$CH$_3$), 3.95 (3H, s, OCH$_3$), 2.86 (3H, s, 3-CH$_3$), 2.75 (3H, s, 4-CH$_3$) and 1.37 (3H, t, OCH$_2$CH$_3$); m/z (%) 314 (57, M$^+$), 268 (100), 240 (18), 209 (19), 195 (25), 181 (52), 154 (42), 127 (28), 77 (26) and 59 (82); and Ethyl 7-methoxycarbonyl-3,4-dimethylpyrrolo[3,2-f]indole-2-carboxylate (isomer II) as colourless solid (0.6027 g, 23.99%) m.p. 197–200° C. (Found: C, 64.82; H, 5.55; N, 8.74. C$_{17}$H$_{18}$N$_2$O$_4$ requires C, 64.92; H, 5.77; N, 8.91%) δH ([$^2$H$_6$]-DMSO 11.37 (1H, s, NH), 8.03 (1H, s, 8-H), 7.58 (1H, d J 3.5, 6-H), 6.88 (1H, d J3.5, 5-H), 4.35 (2H, q, OCH$_2$CH$_3$), 3.99 (3H, s, OCH$_3$), 2.86 (6H, s, 2×CH$_3$), 1.36 (3H, t, OCH$_2$CH$_3$); m/z (%) 314 (53, M$^+$), 268 (100), 240 (13), 209 (21), 195 (12), 181 (12), 154 (13) and 127 (16). Further elution gave 3-acetyl-5-ethoxycarbonyl-2-(1'-methoxycarbonylpyrrol-2'-ylmthyl)-4-methylpyrrole as colourless solid (0.1588 g, 5.98%) m.p. 172–175° C. (FoundL C, 61.38; H, 6.22; N, 8.40. C$_{17}$H$_{20}$N$_2$O$_5$ requires C, 61.43; H, 6.07; N, 8.43%); δH (CDCl$_3$), 9.53 (1H, br s, NH), 7.21 (1H, dd j 3.5 and 2, 5'-H), 6.26 (1H, m, 4'-H), 6.13 (1H, t J 3.5, 3-H), 4.56 (2H, s, CH$_2$), 4.31 (2H, g, OCH$_2$CH$_3$), 3.95 (3H, s, OCH$_3$), 2.59 (3H, s, 4-CH$_3$), 2.47 (3H, s, COCH$_3$), and 1.35 (3H, t, OCH$_2$CH$_3$); m/z (%) 322 (28, M$^+$), 289 (92), 243 (100), 227 (22), 185 (28), 155 (16), 130 (10), 77 (24), 59 (35), 43 (90); 6-(3'-acetyl-5'-ethoxycarbonyl-4'-methylpyrrol-2'-ylmethyl)-2-ethoxycarbonyl-7-methoxycarbonyl-3,4-dimethylbenzo[1,2-b:5,4-b']dipyrrole as off-white solid (0.1593 g, 7.64%) m.p. 218–222° C. (Found: C, 64.19; H, 5.89; N, 7.93. C$_{28}$H$_{31}$N$_3$O$_7$ requires C, 64.48; H, 5.99; N, 8.06%); δH ([$^2$H$_6$]-DMSO) 12.08 (1H, s, pyr-NH), 11.32 (1H, s, 1-NH), 8.01 (1H, s, 8-H), 5.87 (1H, s, 5-H), 4.59 (2H, s, CH$_2$), 4.34 (2H, q, OCH$_2$CH$_3$), 4.28 (2H, q, pyr-CO$_2$CH$_2$CH$_3$), 4.05 (3H, s, OCH$_3$), 2.79 (3H, s, CH$_3$), 2.64 (3H, s, CH$_3$), 2.59 (3H, s, CH$_3$), 2.34 (3H, s, CH$_3$), 1.36 (3H, t, OCH$_2$CH$_3$), 1.33 (3H, t, pyr-OCH$_2$CH$_3$); m/z (%) 521 (2, M$^+$), 478 (3), 432 (2), 386 (2), 370 (2), 355 (3), 342 (2), 300 (2), 193 (2), 179 (2), 105 (2), 91 (3) and 59 (100); and 2,5-di (3'-acetyl-5-ethoxycarbonyl-4-methylpyrrol-2'-ylmethyl)-1-methoxycarbonylpyrrole as colourless crystals after recrystallization from dichloromethane-petroleum ether (0.1292 g, 5.99%) m.p. 227–230° C. (Found: C, 62.27; H, 6.03; N, 7.60. C$_{28}$H$_{33}$N$_3$O$_4$ requires C, 62.32; H, 6.16; N, 7.79%); δH ([$^2$H$_6$]-DMSO) 11.95 (2H, s, 2×NH), 5.19 (2H, s, 3- and 4-H), 4.38 (4H, s, 2×CH$_2$), 4.24 (4H, q, 2×OCH$_2$CH$_3$), 4.01 (3H, s, OCH$_3$), 2.50 (6H, concealed by DMSO, 2×COCH$_3$), 2.28 (6H, s, 2×CH$_3$), 1.29 (6H, t, 2×OCH$_2$CH$_3$); m/z (%) 539 (34, M$^+$), 521 (34), 507 (8), 494 (13), 464 (15), 418 (13), 370 (14), 331 (99), 285 (85), 273 (40), 227 (58), 207 (46), 162 (87) and 59 (100).

(b) Cyclization of 3-acetyl-5-ethoxycarbonyl-2-(1'-methoxy-carbonylpyrrole-2'-ylmethyl)-4-methylpyrrole Toluene-p-sulfonic acid (100 mg) was added to the solution of the 3-acetyl-5-ethoxycarbonyl-2-(1'-methoxycarbonylpyrrol-2'-ylmethyl)-4-methlypyrrole (0.435 g, 1.31 mmol) in benzene (50 cm$^3$), the reaction mixture was heated under reflux for 5 h (using Dean-Stark apparatus). On cooling, the product crystallized, the crystals were filtered and washed with ethanol giving Ethyl 7-methoxycarbonyl-3,4-dimethylpyrrolo[3,2-f]indole-2-carboxylate (isomer II) as colourless crystals (0.3264 g, 79.34%) m.p. 197–200° C. which was identical to the benzo[1,2-b:5,4-b']dipyrrole (isomer II) from the previous experiment by TLC and NMR. Chromatographic separation of the remaining filtrate eluting with (5–0%) petroleum ether in dichloromethane and (0–10%) ethyl acetate in dichloromethane yielded Ethyl 5-methoxycarbonyl-3,4-dimethylpyrrolo[2,3-f]indole-2-carboxylate (isomer I) as colourless solid (0.002 g, 0.49%) which was identical to the pyrrolo[2,3-f] indole (isomer I) from the previous experiment. Also obtained were the pyrrolo[3,2-f]indole (isomer II) (0.0313 g, 7.61%) and the starting 2-pyrrolylmethylpyrrole (0.0125 g, 2.87%).

EXAMPLE 7

Ethyl 3,4-Dimethylpyrrolo[3,2-f]Indole-2-Carboxylate

5% Potassium hydroxide (10 cm$^3$) was added to a solution of ethyl 7-methoxy-3,4-dimethylpyrrolo[3,2-f]indole-2-carboxylate (example 6 isomer II) (0.314 g, 1.0 mmol) in tetrahydrofuran (100 cm$^3$) and the reaction mixture was heated at gentle reflux and stirred for 48 h. After cooling, the reaction mixture was diluted with water (3×50 cm$^3$). The combined extracts were washed with water and then evaporated under reduced pressure to give a yellow solid. This was submitted to column chromatography eluting with (10–25%) ethylacetate and 10% dichloromethane in petroleum ether to give the starting pyrroloindole (0.031 g, 9.87%) and ethyl 3,4-dimethyl pyrrolo[3,2-f]indole-2-carboxylate as a pale green solid (0.169 g, 66.02%) m.p. 233–235° C.; δH (CDCl$_3$) 8.36 (1H, br s, 1-NH), 7.86 (1H, br s, 7-NH), 7.17 (1H, dd J 3.3 and 2.4, 6-H), 7.09 (1H, s, 8-H), 6.62 (1; H, m, 5-H), 4.14 (2H, q, OCH$_2$CH$_3$), 2.96 (3H, s, 3-CH$_3$), 2.94 (3H, s, 4-CH$_3$) and 1.43 (3H, t, OCH$_2$CH$_3$); m/z (%) 256 (28, M$^+$), 227 (5), 210 (100), 181 (99), 168 (28), 154 (89), 140 (15), 126 (63), 77 (42), 63 (32).

Assays for Compound Activity

Assays for cell proliferation/cytotoxy were carried out in tissue culture grade 96 well microtitre plates (Costar). Cells in log growth were added to the plates at a concentration of 1×10$^3$ cells per well on day 0 and serially diluted compounds were then added on day 1. Plates were then incubated at 37° C. in 5% CO$_2$ in air for a further 4 days.

For quantitation of cell growth, the methylene blue biomass staining method was used, the test being read on a Multiscan plate reader at wavelength of 620 nm. The morphology of the cells was checked microscopically under phase-contrast immediately before the fixation and staining with methylene blue, and by ordinary light microscopy thereafter. IC50 values for active compounds were obtained using the computer programme, GS1 and dose-response slopes were also plotted.

When compounds were tested for activity in a colony forming assay the methods used were identical to those described earlier except that serially diluted compound was added to the sloppy agar when the test was set up, and replenished at the same concentration on day 7. The test results were read on day 14.

| RESULTS: | |
|---|---|
| Example Compound | IC50($\mu$M) (HT1080scc2) |
| 1 | 100 |
| 2 | 3 |

What is claimed is:
1. A compound having the formula:

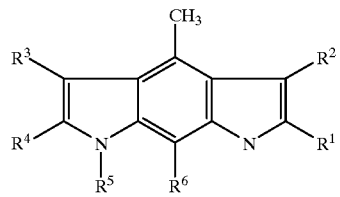

wherein
R$^1$ is COOR$^8$ wherein R$^8$ is alkyl having from 1 to 10 carbon atoms or aralkyl, the aralkyl having from one to four carbon atoms in the alkyl portion and a carbocyclic or heterocyclic group in the aryl portion;
R$^2$ is H, alkyl having from 1 to 10 carbon atoms, or COOR$^7$ wherein R$^7$ is alkyl having from 1 to 10 carbon atoms;
R$^3$ is H, alkyl having from 1 to 10 carbon atoms, or COOR$^8$;
R$^4$ is H, alkyl having from 1 to 10 carbon atoms, or COOR$^8$;
R$^5$ is H, alkyl having from 1 to 10 carbon atoms, aralkyl having from 1 to 4 carbon atoms in the alkyl portion, aryl having from 1 to 10 carbon atoms, acyl having from 1 to 10 carbon atoms, or COOCH$_3$; and
R$^6$ is H or COOCH$_3$;
and salts thereof.

2. A compound (i) having the formula:

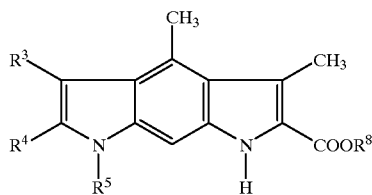

wherein
$R^3$ and $R^4$ selected independently of each other, is H, $CH_3$ or $COOR^9$, except where $R^3$ is $CH_3$, $R^4$ is not $COOC_2H_5$;
$R^5$ is H, $CH_3$, or $COOCH_3$; and
$R^8$ and $R^9$ selected independently of each other is an alkyl having from 1 to 4 carbon atoms or aryl having at least one aromatic ring substituted with one or more groups having from one to ten carbon atoms, or (ii) a salt thereof.

3. The compound according to claim 2, in which $R^3$ and $R^5$ are H.

4. The compound according to claim 3, in which $R^8$ is $C_2H_5$.

5. The compound according to claim 3, in which $R^8$ is benzyl.

6. The compound according to claim 2, in which $R^4$ is $COOR^9$; $R^8$ is $C_2H_5$ or phenyl; and $R^9$ is $CH_3$ or benzyl.

7. The compound according to claim 2, in which $R^5$ is $COOR^9$ and $R^9$ is an alkyl.

8. The compound according to claim 2, in which $R^3$ is $COOR^9$ and $R^4$ is $CH_3$.

9. A compound selected from ethyl 1,7-dihydro-3,4,6-trimethylpyrrolo(3,2f)-indole-2-carboxylate; diethyl 1,7-dihydro-3,4,6-trimethylpyrrolo(3,2-f)indole-2,5-dicarboxylate; ethyl 6-methoxycarbonyl-3,4-dimethyl pyrrolo(3,2-f)indole-2-carboxylate; ethyl 6-benzyloxycarbonyl-3,4-dimethylpyrrolo(3,2-f)indole-2-carboxylate; dibenzyl 3,4-dimethylpyrrolo(3,2-f)indole-2,6-dicarboxylate; ethyl 7-methoxycarbonyl-3,4-dimethyl pyrrolo(3,2-f)indole-2-carboxylate; ethyl 3,4-dimethylpyrrolo(3,2-f)indole-2-carboxylate; and salts thereof.

10. The compound according to claim 2 selected from ethyl 6-benzyloxycarbonyl-3,4-dimethylpyrrolo[3,2f]indole-2-carboxylate; dibenzyl 3,4-dimethylpyrrolo[3,2-f]indole-2,6-dicarboxylate; ethyl 7-methoxycarbonyl-3,4-dimethyl pyrrolo[3,2-f]indole-2-carboxylate; ethyl 3,4-dimethylpyrrolo[3,2-f]indole-2-carboxylate; and a salt thereof.

11. A pharmaceutical composition comprising at least one compound according to claim 1, together with one or more pharmaceutically acceptable diluents, carriers, or excipients.

* * * * *